(12) United States Patent  
Burkhart

(10) Patent No.: US 8,465,522 B2  
(45) Date of Patent: Jun. 18, 2013

(54) SELF-REINFORCING TISSUE FIXATION

(75) Inventor: Stephen S. Burkhart, San Antonio, TX (US)

(73) Assignee: Arthrex, Inc., Naples, FL (US)

( * ) Notice: Subject to any disclaimer, the term of this patent is extended or adjusted under 35 U.S.C. 154(b) by 744 days.

(21) Appl. No.: 12/108,413

(22) Filed: Apr. 23, 2008

(65) Prior Publication Data

US 2008/0262544 A1 Oct. 23, 2008

Related U.S. Application Data

(63) Continuation-in-part of application No. 11/702,621, filed on Feb. 6, 2007, now Pat. No. 7,981,140, which is a continuation-in-part of application No. 11/392,798, filed on Mar. 30, 2006, now Pat. No. 7,803,173.

(60) Provisional application No. 60/666,518, filed on Mar. 30, 2005, provisional application No. 60/913,406, filed on Apr. 23, 2007.

(51) Int. Cl.  
*A61B 17/04* (2006.01)  
*A61B 17/84* (2006.01)

(52) U.S. Cl.  
USPC .......................................... 606/232; 606/300

(58) Field of Classification Search  
USPC ................. 606/213, 215–217, 219, 220, 232, 606/233, 228–231, 300  
See application file for complete search history.

(56) References Cited

U.S. PATENT DOCUMENTS

| | | | | |
|---|---|---|---|---|
| 3,762,418 A | * | 10/1973 | Wasson | 606/226 |
| 6,149,669 A | * | 11/2000 | Li | 606/232 |
| 6,508,830 B2 | * | 1/2003 | Steiner | 606/232 |
| 6,641,596 B1 | * | 11/2003 | Lizardi | 606/232 |
| 6,716,234 B2 | | 4/2004 | Grafton et al. | |
| 7,585,311 B2 | * | 9/2009 | Green et al. | 606/232 |
| 2004/0093031 A1 | | 5/2004 | Burkhart et al. | |
| 2006/0259076 A1 | | 11/2006 | Burkhart et al. | |
| 2007/0135843 A1 | | 6/2007 | Burkhart | |
| 2007/0191849 A1 | | 8/2007 | ElAtreache et al. | |
| 2008/0004659 A1 | | 1/2008 | Burkhart et al. | |

\* cited by examiner

*Primary Examiner* — Julian Woo  
(74) *Attorney, Agent, or Firm* — Dickstein Shapiro LLP

(57) ABSTRACT

Self-reinforcing mechanical systems with application to biological fixation of a first tissue (for example, soft tissue) to a second tissue (for example, bone). As a repair construct is stressed, there is a feedback mechanism (self-reinforcing) against failure that is initially triggered by early failure. The construct "detects" its early/impending failure and utilizes the potentially destructive force to reinforce itself.

9 Claims, 4 Drawing Sheets

SELF-REINFORCING TISSUE FIXATION

CROSS-REFERENCE TO RELATED APPLICATIONS

This is a continuation-in-part of application Ser. No. 11/702,621, now U.S. Pat. No. 7,981,140, filed on Feb. 6, 2007, which is a continuation-in-part of application Ser. No. 11/392,798, now U.S. Pat. No. 7,803,173, filed on Mar. 30, 2006, which claims the benefit of provisional application Ser. No. 60/666,518, filed on Mar. 30, 2005, the entire disclosures of which are incorporated by reference herein. This application also claims the benefit of provisional application Ser. No. 60/913,406 filed on Apr. 23, 2007, the entire disclosure of which is incorporated by reference herein.

FIELD OF THE INVENTION

The present invention relates to self-reinforcing mechanical systems utilizing potentially destructive forces to reinforce themselves, and in particular, to self-reinforcing surgical fixation of tissue to bone using a chain-like serial suture loop construct.

BACKGROUND OF THE INVENTION

The present invention relates to self-reinforcing mechanical systems utilizing potentially destructive forces to reinforce themselves. Non-limiting examples are: 1) Chinese finger trap—the harder you pull against it, the tighter it becomes; and 2) airplane door that is rhomboid-shaped—as a plane gains altitude, the pressure differential between the pressurized cabin and the outside becomes greater, wedging the door for a tighter, more secure construct.

SUMMARY OF THE INVENTION

The present invention applies the self-reinforcing mechanical system described above to biological fixation of a first tissue (for example, soft tissue) to a second tissue (for example, bone). As a repair construct is stressed, there is a feedback mechanism (self-reinforcing) against failure that is initially triggered by early failure. Simply stated, the construct "detects" its early/impending failure and utilizes the potentially destructive force to reinforce itself.

Other features and advantages of the present invention will become apparent from the following description of exemplary embodiments of the invention with reference to the accompanying drawings.

DETAILED DESCRIPTION OF THE PREFERRED EMBODIMENT

Figure 1:
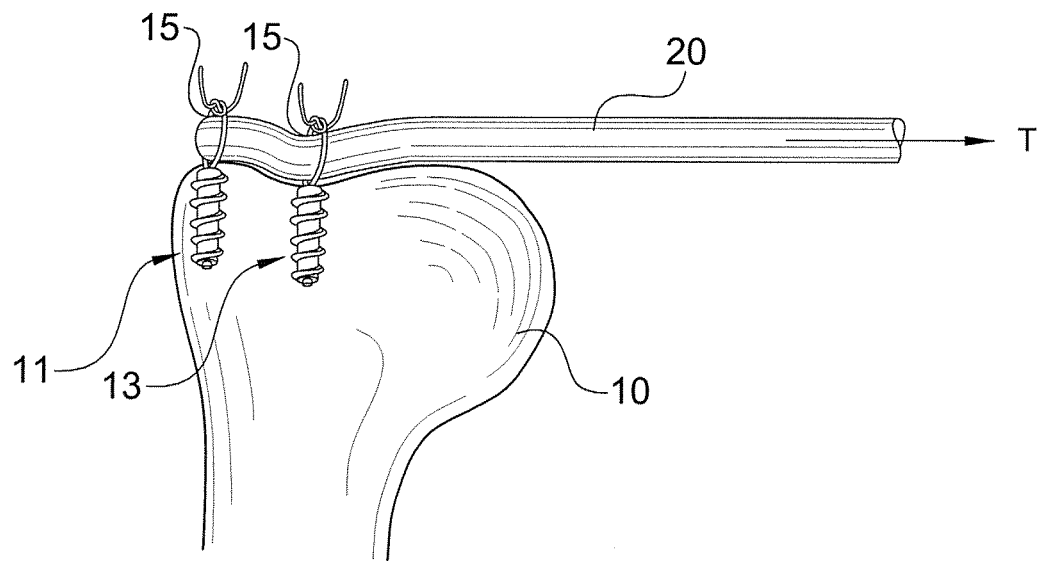
FIG. 1 illustrates a double-row repair construct with sutures.

The present invention provides self-reinforcing mechanical systems and methods for tissue fixation using serial suture loop constructs. The construct 100 preferably includes at least two loops of suture (FiberChain®) 99, preferably high strength suture, as described in U.S. Appl. Publ. No. 2006/0259076, the disclosure of which is incorporated by reference in its entirety herein.

As detailed in U.S. Appl. Publ. No. 2006/0259076, each loop of the serial "chain" preferably has a fixed perimeter. The suture can be interlaced or knotted. The loops may all be similar in size. In an exemplary embodiment, high-strength suture is utilized, such as the high strength suture sold by Arthrex, Inc. of Naples, Fla. under the tradename Fiber-Wire®, which is disclosed and claimed in U.S. Pat. No. 6,716,234, the entire disclosure of which is incorporated herein by reference. FiberWire® suture is formed of an advanced, high-strength fiber material, namely ultrahigh molecular weight polyethylene (UHMWPE), sold under the tradenames Spectra® (Honeywell) and Dyneema® (DSM), braided with at least one other fiber, natural or synthetic, to form lengths of suture material. The preferred FiberWire® suture includes a core within a hollow braided construct, the core being a twisted yarn of UHMWPE. The suture may optionally include filaments of various colors.

The suture chains 99 (FIG. 2) incorporating advanced, high strength materials, such as FiberWire® suture, can be used in demanding orthopedic applications such as shoulder repairs. The suture chains used in the present invention offer surgeons practical means for creating suture constructs of adjustable size without having to tie a knot in situ. The suture chains can be used in a variety of surgical procedures, and most preferably are used to approximate tissue, for example, to approximate torn tendons to bone. Examples of bone anchors used to secure one or more suture chains to bone are threaded anchors, forked suture anchors, swivel anchors (such as an Arthrex SwiveLock™) or press-in anchors (such as the Arthrex Push-Lock™ anchor described in U.S. Patent Application Publication No. 2004/0093031, the disclosure of which is incorporated by reference herein), among many others.

Techniques for knotless fixation of anatomical tissue during surgical applications by employing a chain of suture loops (the FiberChain® technique) have been detailed, for example, in U.S. Appl. Publication No. 2007/0135843 (the disclosure of which is incorporated by reference herein in its entirety), which describes a double-row knotless fixation technique using a chain of suture loops. As detailed in U.S. Appl. Publication No. 2007/0135843, a method for tendon to bone fixation includes, for example, the steps of: (i) providing a first medial row constructed with a first plurality of fixation devices, at least one of the first plurality of fixation devices being an anchor; (ii) providing a second lateral row constructed with a second plurality of fixation devices, at least one of the second plurality of fixation devices being a knotless fixation device; (iii) providing a suture loop construct that includes at least two loops formed of and connected by suture; and (iv) fixating the suture loop construct so that it extends over the soft tissue and is secured in place by at least one of the fixation device of the anchors.

Figure 2:
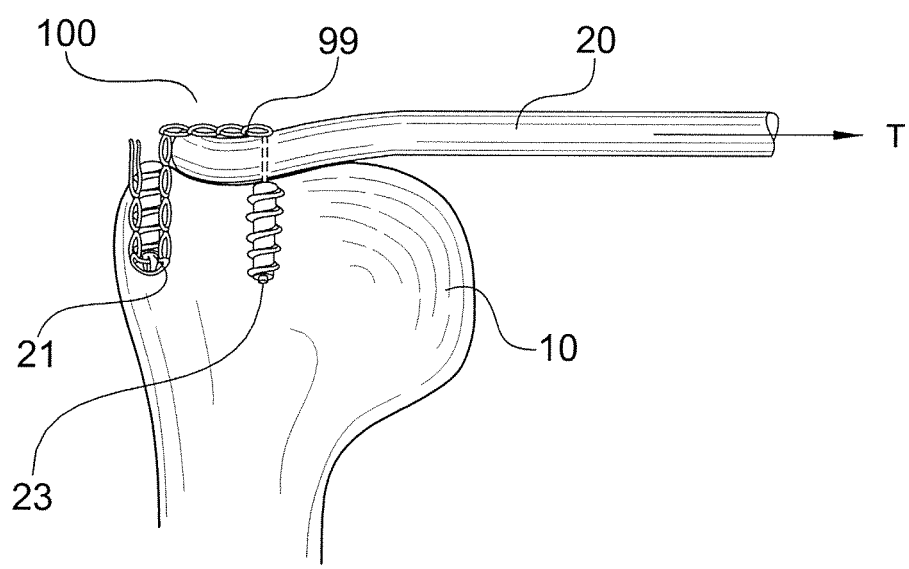
FIG. 2 illustrates a double-row repair construct with Fiber-Chain.

A construct 100 formed by the double-row knotless fixation technique described above, using a chain of suture loops (FiberChain®), is illustrated in FIG. 2. Construct 100 is formed by two lateral rows of FiberChain® 99 that secure a first tissue 20 (for example, rotator cuff 20) to a second tissue 10 (for example, humerus 10). Two fixation devices 21, 23 (for example, a SwiveLock™ anchor 21 and a Biocorkscrew™ anchor 23) fixate the suture loops to the humerus 10.

The mechanism of the present invention which characterizes construct 100 has the following effects:

(i) Elastic deformation of the tendon resulting in a compressive restoring force (normal force relative to the bone surface) which increases the frictional force that is opposing the tensile failure force. The compressive restoring force also creates a "grasping" configuration of tendon indentation to resist slippage.

(ii) Wedge effect of the suture (FiberChain®) against the tendon as the tensile failure force increases.

(iii) Larger surface area of FiberChain® relative to suture to enhance the effects of (i) and (ii).

The Constructs

FIG. 1 illustrates a standard double-row repair with medical mattress sutures 15 and lateral simple sutures 15 with Biocorkscrew™ suture anchors 11, 13.

FIG. 2 illustrates a FiberChain®/SwiveLock™ double-row repair 100.

Modeling the Self-Reinforcing Mechanisms

Figure 3:
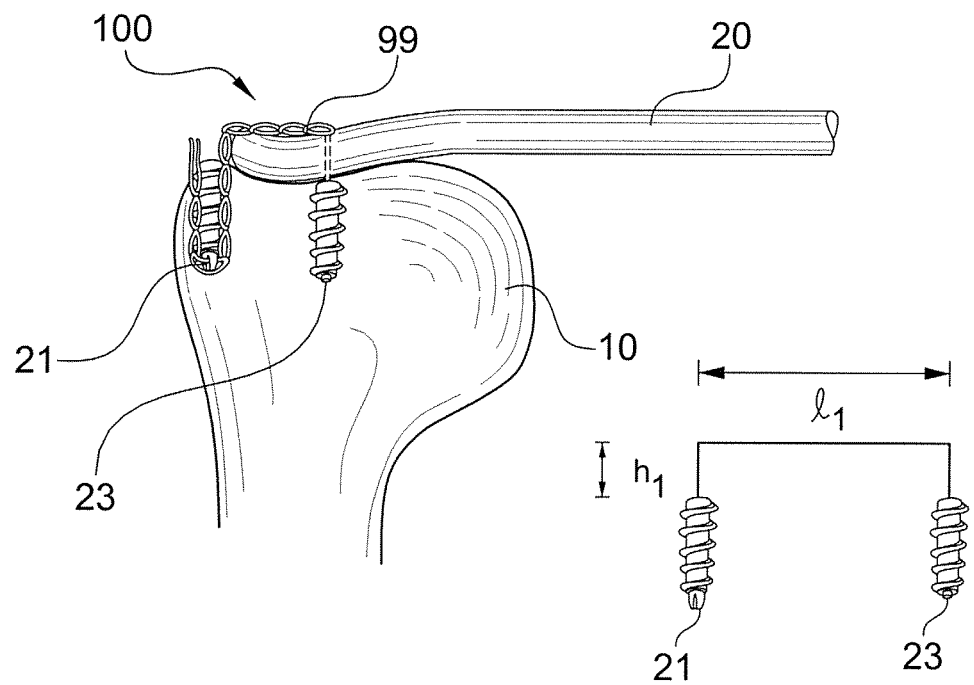
FIG. 3 illustrates a schematic view of a construct A (before loading the tendon)

FIG. 3 is a schematic view of a construct A (before loading the tendon), i.e., construct 100 before loading the tendon 20.

Figure 4:
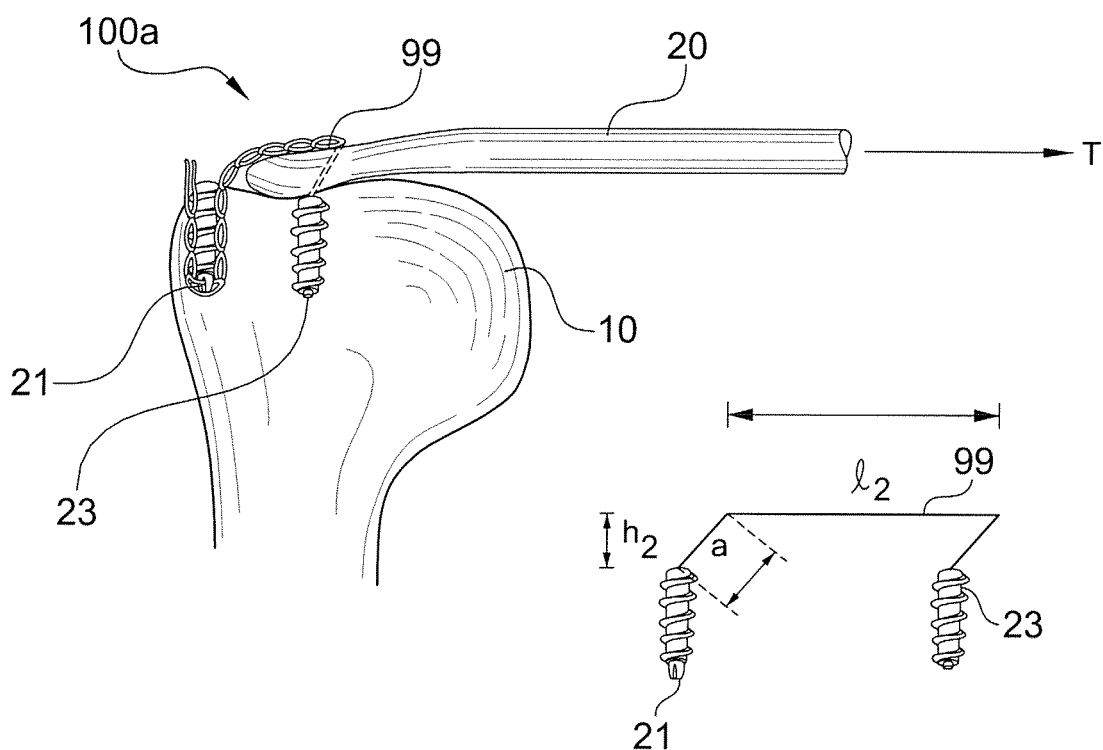
FIG. 4 illustrates a schematic view of a construct B (after loading the tendon)

FIG. 4 is a schematic view of a construct B (after loading the tendon), i.e., construct 100a which is the construct 100 after loading the tendon 20.

Comparing Schematics A and B:

$l_1 = l_2$ (since the point where suture passes through tendon remains the same);

$a = h_1$ (since the total length of suture between the anchors remains the same); and $h_2 < h_1$ (tendon becomes compressed as construct fails).

Consequences of Loading Construct B (110a) (Fiber Chain®/SwiveLock™)

Figure 5A:
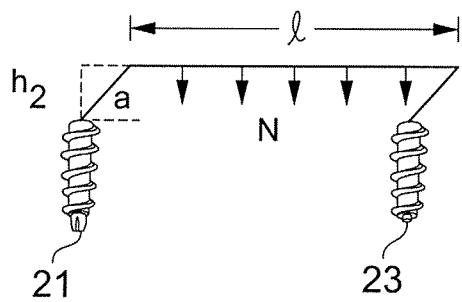
FIGS. 5(a)-(d) illustrate schematic views of the tensile load when the tendon is unloaded, or loaded under different tensile forces (e.g., $T_1$, $T_2$).

1) Tendon 20 becomes elastically compressed under the suture, increasing the distributed normal force N that is perpendicular to bone 10 (FIG. 5(a)).

As the tensile load T increases, the normal force N increases, thereby increasing the frictional resistance to failure, since:

$F = \mu N$, where f = frictional force;

μ = coefficient of friction; and

N = normal force

Figure 5B:
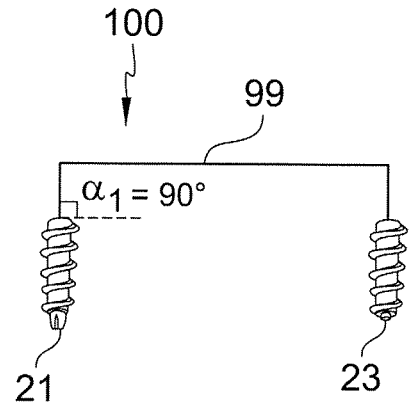
Figure 5C:
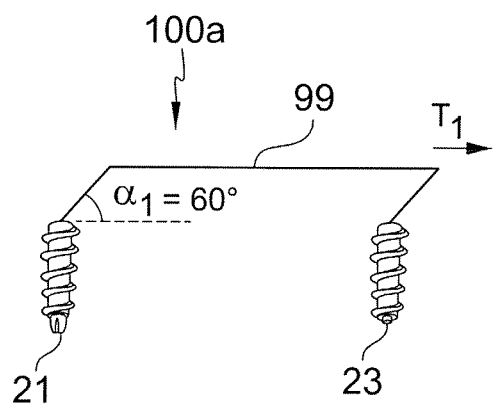
Figure 5D:
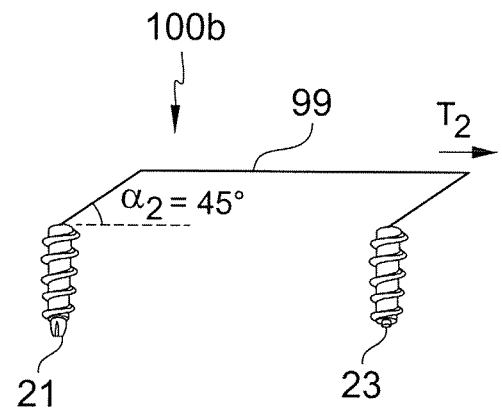

2) Wedge effect of tendon 20 under suture 99—suture wedges tendon more tightly underneath it as load increases and angle α decreases (FIGS. 5(b)-(d)).

3) Larger surface area of FiberChain® 99 (compared to suture) augments the effects of 1) and 2) above.

Tests Conducted

Biomechanical tests were conducted wherein failure modes and parameters for double-row FiberChain®/SwivelLock™ rotator cuff repair were compared to the same parameters in standard double-row rotator cuff repair. The repairs were cyclically loaded from 10 to 100N at 1 Hz for 500 cycles and the elongation (gapping) at the repair site was measured. A single-cycle pull to failure was then conducted to measure yield load and ultimate load. The elongation (gapping) was 3.2 mm. for SwiveLock™ and 2.1 mm. for standard double-row (slightly greater gapping for SwiveLock™, though not statistically significant). However, the ultimate load to failure for the SwiveLock™ system was greater (539N) than that of the standard double-row (511N). This implies an inherent quality in the FiberChain®/SwiveLock™ construct that "detects" its early failure and self-reinforces to achieve a higher ultimate load to failure.

Additional Applications

Figure 6A:
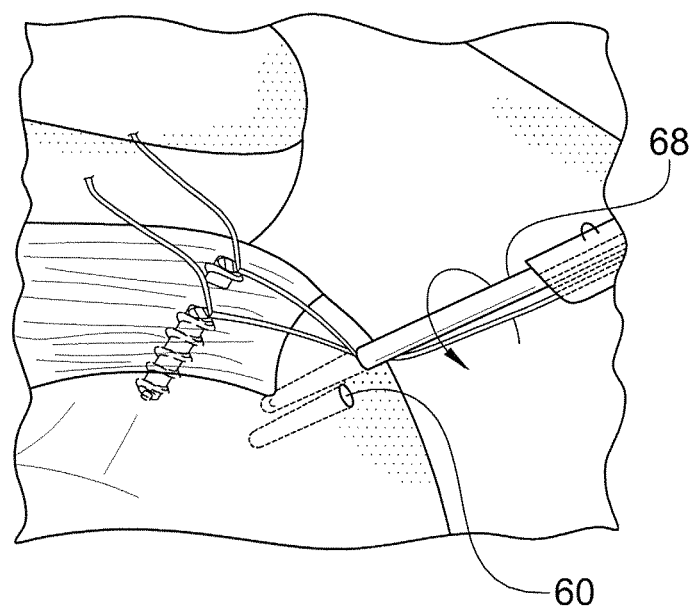
FIGS. 6(a) and 6(b) show the Suture Bridge™ and Speed-Bridge™ fixation techniques.
Figure 6B:
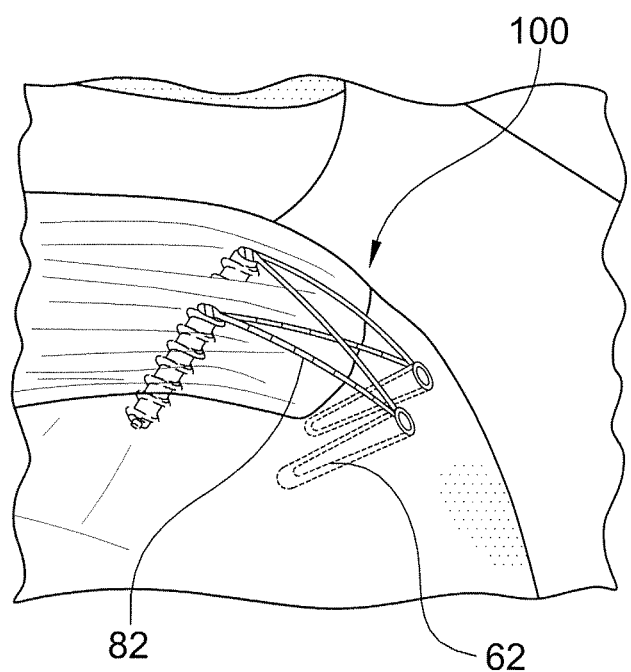

1) By the same mechanisms (1 and 2), the Suture Bridge™ technique (with FiberWire® and PushLock™ and Biocorkscrew™ anchors), which is described in U.S. Application Publication No. 2007/0191849, and the SpeedBridge™ technique (with FiberTape™ and SwiveLock C™ anchors), which is described in U.S. application Ser. No. 12/043,008, filed on Mar. 5, 2008 (the entire disclosures of these two applications being herein incorporated by reference) should operate under the same self-reinforcing mechanisms. FIGS. 6(a) and 6(b) show these techniques, wherein the hole in bone is identified by reference number 60, the anchors are indicated by reference number 62, the suture or tape is indicated by reference number 82, and the construct is represented generally by reference number 100.

2) Running side-to-side suture would have a similar self-reinforcing mechanisms, especially when the terminal free end is anchored to bone (as in the FiberChain® technique).

3) These mechanisms apply to all fixation of soft tissue to bone in all joints.

Comparison to Standard Double-Row Repair

The standard double-row construct has suture loops that are maximally tightened when the knots are tied so there are no additional degrees of freedom (i.e., no slack). Accordingly, it has no capacity to develop further compression of tendon as load is applied and therefore cannot be self-reinforcing.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed is:

1. A method of reinforcing soft tissue fixation to bone, comprising the steps of:

forming a soft tissue fixation construct comprising a flexible strand passing over a soft tissue to be fixated by threading one end of a flexible strand through an eyelet of a first fixation device located at a distal end of the first fixation device, subsequently attaching the one end of the flexible strand in a bone and not under the soft tissue using at least the first fixation device, subsequently passing the flexible strand over the soft tissue and the bone, and then attaching the other end of the flexible strand in the bone and under the soft tissue using at least a second fixation device, resulting in three rectilinear fixation forces, from the distal end of the first fixation device, vertically up to the soft tissue, laterally across the soft tissue, and vertically down to the second fixation device; and loading the fixation construct under a lateral tensile force along three linear portions of the flexible strand by pulling the soft tissue laterally, the lateral tensile force being translated by the fixation construct into a force normal to the soft tissue, resulting in a wedge effect of fixation forces, on the tissue from the distal end of the first fixation device, up at an angle to vertical to the tissue, laterally across the tissue with a force normal to the tissue in a downward direction, and down at an angle to the second fixation device, thereby self-reinforcing the fixation construct by increasing the normal force to the soft tissue and increasing, therefore, the frictional resistance to failure.

2. The method of claim 1, wherein the soft tissue is a torn tendon or ligament.

3. The method of claim 1, wherein the flexible strand is a suture, a suture chain comprising a plurality of suture loops formed of interlaced or knotted suture, or a suture tape.

4. The method of claim 1, wherein at least one of the first and second fixation devices is a knotless anchor.

5. A method of reinforcing soft tissue fixation to bone, comprising the steps of:
providing a suture chain comprising a plurality of suture loops formed of interlaced or knotted suture;
providing a first fixation device pre-loaded with the suture chain by threading one end of the suture chain through an eyelet of the first fixation device, the eyelet being located at a distal end of the first fixation device;
securing the first fixation device pre-loaded with the suture chain in bone and not under soft tissue to be fixated;
subsequently, passing the suture chain over the soft tissue to be fixated to form a suture construct, and then attaching the other end of the suture chain in the bone and under the soft tissue using at least a second fixation device, resulting in three rectilinear fixation forces, from the distal end of the first fixation device, vertically up to the soft tissue, laterally across the soft tissue, and vertically down to the second fixation device; and
loading the suture construct under a lateral tensile force along three linear portions of the flexible strand by pulling the soft tissue laterally, the lateral tensile force being translated by the suture construct into a force normal to the soft tissue, resulting in a wedge effect of fixation forces, on the tissue from the distal end of the first fixation device, up at an angle to vertical to the tissue, laterally across the tissue with a force normal to the tissue in a downward direction, and down at an angle to the second fixation device, thereby self-reinforcing the suture construct by increasing the normal force to the soft tissue and increasing, therefore, the frictional resistance to failure.

6. The method of claim 5 wherein the increase in the normal force to the soft tissue resulting from loading of the suture under a tensile force elastically compresses and deforms the soft tissue, which in turn increases the frictional force of the suture chain relative to the soft tissue.

7. The method of claim 5 wherein, when the soft tissue is pulled laterally, the angle between the normal force and a tensile load decreases from a first angle of about 90 degrees to a second angle.

8. The method of claim 7, wherein the second angle is about 60 degrees.

9. The method of claim 7, wherein the second angle is about 45 degrees.

* * * * *